United States Patent [19]

Ohsumi et al.

[11] Patent Number: 5,405,644
[45] Date of Patent: Apr. 11, 1995

[54] PROCESS FOR PRODUCING ANTIMICROBIAL FIBER

[75] Inventors: Shuichi Ohsumi, Osaka; Hideki Kato, Kuwana, both of Japan

[73] Assignee: Toagosei Chemical Industry Co., Ltd., Tokyo, Japan

[21] Appl. No.: 145,211

[22] Filed: Nov. 3, 1993

[30] Foreign Application Priority Data

Nov. 17, 1992 [JP] Japan .................................. 4-331028

[51] Int. Cl.$^6$ ...................... B05D 1/00; D01D 10/00; D01F 1/00
[52] U.S. Cl. ..................... 427/2.31; 427/2.1; 427/434.2; 427/434.6; 106/15.05; 428/375; 428/378; 428/389; 428/392; 428/396; 424/618; 424/619
[58] Field of Search ............. 106/15.05; 428/375, 428/378, 389, 392, 396; 424/618, 619; 427/2.1, 2.31, 434.2, 434.6

[56] References Cited

U.S. PATENT DOCUMENTS

| | | | |
|---|---|---|---|
| 4,708,870 | 11/1987 | Pardini | 424/81 |
| 4,835,019 | 5/1989 | White et al. | 428/279 |
| 4,842,932 | 6/1989 | Burton | 428/375 |
| 4,938,955 | 7/1990 | Niira et al. | 424/79 |
| 5,047,448 | 9/1991 | Tanaka et al. | 428/397 |
| 5,135,811 | 8/1992 | White et al. | 428/395 |
| 5,264,250 | 11/1993 | Steele et al. | 106/15.05 |

FOREIGN PATENT DOCUMENTS

| | | | |
|---|---|---|---|
| 3-14612 | 1/1991 | Japan | 106/15.05 |
| 03-130465 | 6/1991 | Japan | 106/15.05 |
| 03-130466 | 6/1991 | Japan | 106/15.05 |
| 03-213509 | 9/1991 | Japan | 106/15.05 |
| 04-202849 | 7/1992 | Japan | 106/15.05 |

OTHER PUBLICATIONS

Chemical Abstracts, vol. 116 (1992), p. 56. Abstract No. 60818w. [no month].

*Primary Examiner*—Anthony Green
*Attorney, Agent, or Firm*—Browdy and Neimark

[57] ABSTRACT

A process for producing an antimicrobial fiber having a silver-containing inorganic microbicide characterized by using a treating solution for producing said fiber which contains a discoloration inhibitor represented by the following general formula:

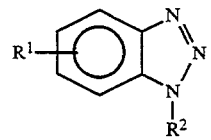

wherein $R^1$ is hydrogen or a lower alkyl group and $R^2$ is hydrogen or an alkali metal.

8 Claims, No Drawings

PROCESS FOR PRODUCING ANTIMICROBIAL FIBER

The present invention relates to a process for producing an antimicrobial fiber having a silver-containing inorganic microbicide, which antimicrobial fiber causes no discoloration during or after its treatment steps wherein the antimicrobial fiber is treated with various treating solutions.

The antimicrobial fiber obtained by the present process causes no discoloration due to use of various treating solutions during or after its production steps and has an excellent antimicrobial property. It is therefore useful not only as a single fiber but also as a material for various fiber products such as clothing (e.g. socks, stockings and underwear), bedding (e.g. bedcover and sheet), protective articles (e.g. mask and bandage) and the like.

A number of microbicides have been proposed which can exhibit an antimicrobial property when incorporated in fibers, coatings, shaped resin articles, papers, binders, etc. Among them, inorganic microbicides have drawn special attention in recent years, because of their excellent durability.

Most of the inorganic microbicides are microbicides obtained by supporting silver ion as a component for antimicrobial property on an inorganic compound by various methods (these inorganic microbicides are hereinafter referred to simply as microbicides). The inorganic compound on which silver ion is to be supported, includes, for example, active carbon, apatite, zeolite and phosphates.

A fiber having a microbicide (this fiber is hereinafter referred to as antimicrobial fiber) is subjected, during the spinning process, to various treating steps such as drawing, scouring, dyeing, bleaching, mixed fiber spinning, weight reduction and the like, and is treated with various treating solutions such as textile oil, aqueous alkali solution, bleaching agent, detergent and the like. In the treatment, the silver ion contained in the microbicide dissolves in the treating solutions in a very small amount or reacts with certain components of the treating solutions, whereby the antimicrobial fiber is discolored.

Meanwhile, in order to prevent a microbicide-containing resin from being discolored, there have been made proposals of adding a stabilizer to the resin to allow the resin to contain a microbicide and a stabilizer together. For example, as stabilizers for antimicrobial resin compositions each comprising (a) an antimicrobial zeolite having silver ion supported thereon and (b) a resin, there are benzotriazole compounds, oxalic acid anilide compounds, salicylic acid compounds, hindered amine compounds and hindered phenol compounds (Japanese Patent Kokai No. 63-265958).

When each of these stabilizers is added to a resin for fiber production and the resin is spun into an antimicrobial fiber, however, it is impossible to suppress the discoloration of the antimicrobial fiber sufficiently when the antimicrobial fiber is treated with various treating solutions in the treating steps or when the spinning solution used for production of the antimicrobial fiber contains a large amount of a solvent. Hence, it has been desired to develop a process for producing an antimicrobial fiber which causes no discoloration in various fiber treatment steps.

The present invention is intended to provide a process for producing an antimicrobial fiber having a microbicide and having an excellent antimicrobial property, which fiber causes, during or after the production, substantially no discoloration induced by use of treating solutions or by the spinning solution per se.

The present inventors made an extensive research in order to achieve the above task and found that the addition of a discoloration inhibitor comprising a particular compound to various treating solutions is very effective. The finding has led to the completion of the present invention.

The present invention resides in a process for producing an antimicrobial fiber having a silver-containing inorganic microbicide characterized by using a treating solution for producing said fiber which contains a discoloration inhibitor represented by the following general formula:

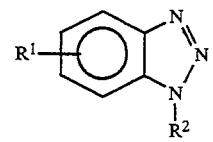

wherein $R^1$ is hydrogen or a lower alkyl group and $R^2$ is hydrogen or an alkali metal.

The present invention is described in detail below.

[Raw materials for antimicrobial fiber]

Base fiber

The base fiber used in the present invention can be any natural or chemical fiber. The natural fiber includes, for example, vegetable fibers such as cotton, hemp, flax, coconut, rush and the like; animal fibers such as wool, goat hair, mohair, cashmere, camel hair, silk and the like; and mineral fibers such as asbestos and the like. The chemical fiber includes, for example, inorganic fibers such as rock fiber, metal fiber, graphite fiber, silica fiber, titanate fiber and the like; cellulose fibers such as viscose fiber, cuprammonium fiber and the like; protein fibers such as casein fiber, soybean fiber and the like; regenerated or semisynthetic fibers such as regenerated silk yarn, alginate fiber and the like; and synthetic fibers such as polyamide fiber, polyester fiber, polyvinyl fiber, polyacrylic fiber, polyurethane fiber, polyethylene fiber, polyvinylidene fiber, polystyrene fiber and the like.

Microbicide

The microbicide used in the present invention can be any inorganic compound having silver ion supported thereon. The inorganic compound on which silver ion is to be supported, includes the followings, for example. That is, inorganic adsorbents such as active carbon, active alumina, silica gel and the like; and inorganic ion exchangers such as zeolite, hydroxyapatite, zirconium phosphate, titanium phosphate, potassium titanate, antimony oxide hydrate, bismuth oxide hydrate, zirconium oxide hydrate, hydrotalcite and the like.

The method for supporting silver ion on such an inorganic compound is not particularly restricted. There are various specific methods for supporting, such as (1) a method by physical or chemical adsorption, (2) a method by ion exchange reaction, (3) a method by using a binder, (4) a method by striking a silver compound into an inorganic compound, and (5) a method by forming a thin layer of a silver compound on the surface of an inorganic compound by a thin-film formation technique such as vapor deposition, dissolution and precipitation, sputtering or the like.

Among the above-mentioned inorganic compounds, inorganic ion exchangers are preferable because silver ion is fixed thereon strongly. Among the inorganic ion exchangers, particularly preferable is a tetravalent metal phosphate represented by the following general formula [1]:

$$M^1{}_aM^2{}_2(PO^4)_3 \cdot nH_2O \qquad [1]$$

wherein $M^1$ is at least one ion having a valence of m, selected from alkali metal ions, alkaline earth metal ions, ammonium ion and hydrogen ion; $M^2$ is a tetravalent metal such as Ti, Zr, Sn or the like; n is a number satisfying $0 \leq n \leq 6$; and a is a positive number satisfying $ma = 1$.

The tetravalent-metal phosphate is a crystalline compound belonging to the space group R3c, and the constituent ions form a three-dimensional network structure.

In the present invention, the microbicide is preferably one which is obtained by supporting silver ion on a tetravalent-metal phosphate represented by the general formula [1] and which is represented by the following general formula [2]:

$$Ag_pM^1{}_qM^2{}_2(PO_4)_3 \cdot nH_2O \qquad [2]$$

wherein $M^1$, $M^2$ and n are the same as defined above; p and q are positive numbers satisfying $p + mq = 1$ (m is a valence of $M^1$).

Specific examples of the microbicide represented by the general formula [2] are shown below.

$Ag_{0.005}Li_{0.995}Zr_2(PO_4)_3$
$Ag_{0.01}(NH_4)_{0.99}Zr_2(PO_4)_3$
$Ag_{0.05}Na_{0.95}Zr_2(PO_4)_3$
$Ag_{0.2}K_{0.8}Ti_2(PO_4)_3$
$Ag_{0.1}H_{0.9}Zr_2(PO_4)_3$
$Ag_{0.05}H_{0.05}Na_{0.90}(PO_4)_3$
$Ag_{0.20}H_{0.20}Na_{0.60}Zr_2(PO_4)_3$
$Ag_{0.05}H_{0.55}Na0.40Zr_2(PO_4)_3$

A fiber having a microbicide of the general formula [2] causes only slight discoloration when treated with various treating solutions mentioned later but, when said treating solutions or the spinning solution of said fiber contains a discoloration inhibitor of the present invention, surprisingly causes no discoloration.

The tetravalent-metal phosphate can be synthesized by firing process, wet process, hydrothermal process, etc. For example, a tetravalent-metal phosphate wherein the tetravalent metal is zirconium, can be easily obtained as follows by a wet process.

Oxalic acid and phosphoric acid are added, in this order, to an aqueous solution of zirconium oxynitrate and sodium nitrate, with stirring. The mixture is adjusted to pH 3.5 with an aqueous sodium hydroxide solution and then refluxed under heating for 78 hours. The resulting precipitate is collected by filtration, water-washed, dried and disintegrated to obtain a zirconium phosphate [$NaZr_2(PO_4)_3$] having a network structure.

The zirconium phosphate is immersed in an aqueous solution containing an appropriate concentration of silver ion, whereby a microbicide of the general formula [2] is obtained.

In order to obtain a microbicide of the general formula [2] having high antifungal, antibacterial and antialgal properties, p in the general formula [2] is desirably large. However, when p is 0.001 or larger, sufficient antifungal, antibacterial and antialgal properties can be obtained. When p is smaller than 0.001, it may be difficult to obtain antifungal, antibacterial and antialgal properties over a long period of time. In view of this and economy, p is preferably in the range of 0.01-0.5.

An antimicrobial fiber can be obtained by supporting the above-mentioned microbicide on or in the above-mentioned base fiber. The method for supporting has no particular restriction. The supporting method can be exemplified by a method which comprises kneading a resin to be made into a fiber and a microbicide and subjecting the mixture to spinning, and a method which comprises applying a microbicide mixed with a binder, to the surface of a spun fiber by coating, dipping or the like.

[Treating solutions]

The treating solutions used in the present process refers to those which are used for producing an antimicrobial fiber in the spinning step to the finishing step of fiber production, and which have a feature in that they contain a particular discoloration inhibitor represented by the general formula [3] shown later.

Incidentally, the antimicrobial fiber of the present invention refers not only to a fiber obtained by a spinning step but also to a fiber precursor immediately after being taken out of a spinning nozzle.

Each of the treating solutions used in the present process can contain various components conventionally used for the efficient operation of each treating step.

The treating steps actually employed are appropriately selected depending upon the kind of the fiber produced. They include, for example, spinning step, cotton spinning step, silk reeling step, wool scouring step, drawing step, decolorization step, twisting step, cutting step, washing step, weaving and knitting step, bleaching step, dyeing step, sizing and desizing step, printing step, dyeing-by-dipping step and weight reduction step.

The treating solutions typically used in these treating steps are an oil for spinning or weaving, a detergent, a dyeing assistant, a finishing agent and an aqueous alkali solution used in weight reduction step. Specific examples thereof are as follows.

That is, the oil for spinning or weaving includes oil for chemical fiber, oil for worsted spinning, oil for woolen spinning, oil for hard and bast fiber spinning, oil for synthetic fiber spinning, sizing agent and oil for hank yarn, sizing agent and oil, oil for general fabric, oil for silk yarn spinning, etc. The detergent includes desizing assistant and detergent for cotton, detergent for grease wool, unwinding agent for cocoon, bleaching assistant, mercerization assistant, assistant for carpet weaving, degreasing agent for grease wool, desizing and detergent for staple fiber, silk, hemp or synthetic fiber, etc. The dyeing assistant includes dyeing assistant for wool, dyeing assistant for cotton or staple fiber, dyeing assistant for acetate, dyeing assistant for polyamide fiber, dyeing assistant for polyacrylic (mixed) fiber, dyeing assistant for polyester (mixed) fiber, printing assistant, etc. The finishing agent includes softening agent for synthetic fiber or mixed fiber, resin finishing agent, agent for water resistance or oil resistance, antistatic agent, etc.

Each of these treating solutions is ordinarily a mixture of some components including a surfactant and/or an alkaline compound. Typical examples of the components are as follows. (Alkaline compound): sodium hydroxide, sodium carbonate, potassium carbonate, sodium bicarbonate, sodium sesquicarbonate, soda ash, sodium silicate, slaked lime, ammonia water, etc.

(Organic solvent): benzine, kerosene, naphtha, etc.

(Soap): soaps such as laurate, myristate, palmitate, stearate, oleate soaps and the like; solvent-containing soaps; organic base soaps such as ethanolamine soap, cyclohexylamine soap, alkylamine soap and the like; and so forth.

(Dispersant or surfactant): alkylaryl sulfonation products and higher sulfonic acid oil; alkylsulfonic acids, olefinsulfonic acids, alkylbenzenesulfonic acids, naphthalenesulfonic acid and salts thereof; alkyl ether sulfates, alkylamide sulfates, sulfonated oils, vegetable oil sulfates, higher aliphatic alcohol sulfates and salts of higher alcohol sulfates; condensation products of fatty acids; proteins and aliphatic condensation products; salts of phosphoric acid esters, such as salts of alkyl phosphates, salts of alkyl ether phosphates and the like; acylated peptides and carboxylic acid salts such as salts of alkyl ether carboxylates and the like; aliphatic amine salts, aliphatic quaternary ammonium salts, aromatic quaternary ammonium salts and heterocyclic quaternary ammonium salts; imidazoline derivatives, aminocarboxylic acid salts and betaine; ethylene oxide condensation products, condensation products between oleic acid and aminosulfonic acid and condensation products between fatty acid and protein; and so forth.

(Reducing agent): sulfurous acid gas, sodium sulfite, zinc powder, Candit V, grape sugar, etc.

(Oxidizing agent): aqueous hydrogen peroxide solution, sodium peroxide, sodium hypochlorite, potassium permanganate, chrolamine TO, etc.

(Enzyme): animal enzymes such as pancreatin, trypsin, Fermasol and the like; and vegetable enzymes such as malt enzymes (e.g., Amiladine, Brimal and Dextose) and bacterial enzymes (e.g., Biolase and Rapidase).

(Others): higher alcohols, animal or vegetable waxes, mineral waxes, vegetable oils, mineral oils, methyl esters of vegetable oils, liquid paraffin, etc.

Discoloration Inhibitor

The discoloration inhibitor used in the present process is a compound represented by the following general formula [3]

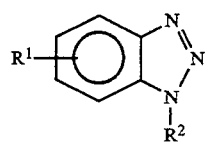

[3]

wherein $R^1$ is hydrogen or a lower alkyl group and $R^2$ is hydrogen or an alkali metal.

When $R^1$ is a lower alkyl group, the lower alkyl group is exemplified by methyl, ethyl, n-propyl, isopropyl and butyl. Methyl is particularly preferable because the compound of the general formula [3] wherein $R^1$ is methyl, has high stability.

When $R^2$ is an alkali metal, the alkali metal is exemplified by lithium, sodium, potassium and cesium.

Preferable examples of the compound of the general formula [3] are methylbenzotriazole and the potassium salt thereof.

Benzotriazole type compounds have been known as a resin stabilizer. In the present invention it has been found that when, among various benzotriazole type compounds, any of the above particular compounds of the general formula [3] is added to a treating solution for fiber and the resulting treating solution is used for treatment of an antimicrobial fiber having a silver ion-containing microbicide, the antimicrobial fiber after the treatment causes substantially no discoloration. This fact is quite surprising.

The amount of the discoloration inhibitor used in the treating solution is preferably 0.005–5 parts by weight (parts by weight are hereinafter referred to simply as parts), more preferably 0.05–0.5 part per 100 parts of the treating solution. When the amount is smaller than 0.005 part, it may be impossible to sufficiently suppress the discoloration of the antimicrobial fiber. Meanwhile, when the amount is larger than 5 parts, there is seen substantially no higher effect on suppression of discoloration and rather such an amount may give an unfavorable influence on the expected effect of each treating solution.

The discoloration inhibitor of the present invention can exhibit an especially striking effect when used in a treating solution containing a surfactant and/or an alkaline compound in a high concentration, for example, an oil for spinning or an alkaline detergent.

Preparation of Treating Solutions

Each of the treating solutions used in the present process can be easily prepared by mixing or kneading the above discoloration inhibitor (a benzotriazole type compound) with a treating solution under a temperature and a pressure appropriately selected (if necessary, heating and increasing or decreasing of pressure are employed) in view of the properties of the fiber to be treated. The specific operations for the above preparation can be conducted in an ordinary manner.

The benzotriazole type compounds used in the present process include hydrophilic ones and oleophilic ones. Hence, a benzotriazole type compound highly soluble or dispersible in the treating solution to be used must be appropriately selected in order to obtain a sufficient effect for suppression of discoloration.

In preparing a treating solution used in the present process, a discoloration inhibitor of the present invention is incorporated at an appropriate concentration in a conventional treating solution (composition) such as oil for spinning, mercerization assistant, finishing agent or the like. Examples of such formulations are shown below. (In the followings, R is an alkyl group; n is a positive number; and each amount used refers to parts by weight.)

| | Parts used |
|---|---|
| (Oil for spinning) | |
| 1. Ultrafine particle colloidal silica | 100 |
| $RN^+[(C_2H_4O)_nH]_2CH_2COO^-$ | 50 |
| Benzotriazole type compound (discoloration inhibitor) | 2.0 |
| 2. R—O(CH$_2$CH$_2$O)$_n$H | 100 |
| R—OSO$_3$Na | 35 |
| R—COOR(OH)$_2$ | 25 |
| Higher alcohol | 10 |
| Mineral oil | 10 |

|  | Parts used |
|---|---|
| Benzotriazole type compound (discoloration inhibitor) | 1 |
| Water | 50 |
| 3. Esterified oil | 100 |
| Liquid paraffin | 60 |
| R—O(CH$_2$CH$_2$O)$_n$H | 40 |
| Benzotriazole type compound (discoloration inhibitor) | 0.6 |
| (Sizing agent and oil) | |
| 4. Aqueous polyacrylic acid solution | 100 |
| Benzotriazole type compound (discoloration inhibitor) | 0.3 |
| 5. RO(C$_2$H$_4$O)$_n$H sulfonated sperm oil | 30 |
| Neutral paraffin wax | 100 |
| Benzotriazole type compound (discoloration inhibitor) | 0.3 |
| (Marcerization assistant) | |
| 6. 25° Be' sodium hydroxide | 100 |
| ROSO$_3$Na | 0.15 |
| Benzotriazole type compound (discoloration inhibitor) | 0.3 |
| Water | 0.35 |
| (Washing agent for woolen cloth) | |
| 7. R—C$_6$H$_{10}$O—(C$_2$H$_4$O)$_n$H | 0.1 |
| Higher alcohol detergent | 0.2 |
| Soda ash | 0.1 |
| Benzotriazole type compound (discoloration inhibitor) | 0.4 |
| Water | 100 |
| (Dyeing assistant) | |
| 8. ROSO$_3$Na | 15 |
| Dichlorobenzene | 100 |
| Benzotriazole type compound (discoloration inhibitor) | 0.5 |
| Water | 40 |
| (Finishing oil agent) | |
| 9. Lanolin | 50 |
| RCOO(CH$_2$CH$_2$O)$_n$H | 100 |
| Polyamine derivative | 70 |
| Benzotriazole type compound (discoloration inhibitor) | 1.5 |
| (Antistatic agent) | |
| 10. Salt of alkyl phosphate | 100 |
| Benzotriazole type compound (discoloration inhibitor) | 0.5 |

[Preparation of Antimicrobial Fiber]

In producing an antimicrobial fiber according to the present process, there is no particular restriction to the spinning method, and a spinning method suitable for the specific fiber to be produced can be appropriately selected from conventional spinning methods, i.e. basic spinning methods (e.g. melt spinning, wet spinning and dry spinning), emulsion spinning method, conjugate spinning method, spinning methods using no spinning nozzle (e.g., spinning method comprising cutting of drawn thin film, drawing and heat setting, spinning method by drawing of a rod-like polymer, and spinning method by interfacial polymerization), and the like.

When a polymer material already containing a microbicide is subjected to wet spinning (in this case, said polymer material is dissolved in a solvent and the solution is used as a spinning solution) or to dry spinning, there is a high risk of microbicide discoloration. In order to prevent it, the spinning solution can contain a discoloration inhibitor of the present invention.

The amount of the discoloration inhibitor of the general formula [3] used in the treating solution is preferably 0.005–5 parts, more preferably 0.05–0.5 parts per 100 parts of the treating solution. When the amount is smaller than 0.005 part, it may be impossible to sufficiently suppress the discoloration of the antimicrobial fiber. Meanwhile, when the amount is larger than 5 parts, there is seen substantially no higher effect on suppression of discoloration, and rather such an amount may give an unfavorable influence on the expected effect of each treating solution.

In treating an antimicrobial fiber with a treating solution containing a particular discoloration inhibitor according to the present process, there is no particular restriction to the treatment, and the treatment can be conducted in the same manners as in the treatment steps conventionally used in fiber production.

A treating solution containing a discoloration inhibitor gives no unfavorable influence on the antimicrobial fiber to be produced, during and even after fiber production. It is therefore not necessary to completely remove, by washing, the treating solution remaining on the fiber. Rather, the presence of a small amount of the discoloration inhibitor on the surface of the antimicrobial fiber can effectively prevent the possible discoloration of the antimicrobial fiber due to its contact with a discoloration-inducing substance or the like.

According to the process of the present invention, the antimicrobial fiber having a silver ion-containing microbicide causes no discoloration by use of various treating solutions during fiber production; and further the antimicrobial fiber after the treatment causes no discoloration over a long period of time even in a severe environment and maintains antifungal, antibacterial and antialgal properties.

[Applications]

The antimicrobial fiber obtained by the present process, having an excellent antimicrobial property and moreover being free from discoloration, can be used widely in various applications. It has a particular advantage of maintaining whiteness and cleanness and can be used, for example, in the following specific applications. That is, clothing such as socks, stockings, underwear and the like; bedding such as bedcover, sheet and the like; protective articles such as mask, bandage and the like; textile products such as towel and the like; hairs for brushes; fishing nets; and so forth.

The present invention is described in more detail below by way of Examples.

Referential Example 1 [Preparation of Microbicides]

An aqueous zirconium sulfate solution and an aqueous sodium dihydrogenphosphate solution were mixed so as to give the ratio of zirconium to phosphorus of 2:3, whereby a precipitate was formed. The mixture was adjusted to pH 2 with an aqueous sodium hydroxide solution and then placed in a hydrothermal state at 150° C. for 24 hours, whereby crystalline zirconium phosphate was obtained.

The zirconium phosphate was added to an aqueous solution of silver nitrate and nitric acid. The mixture was stirred at room temperature for 4 hours, then washed with water thoroughly and dried. The resulting material was fired at 750° C. for 4 hours, followed by disintegration to obtain a microbicide "a" as white powders having an average particle diameter of 0.47 μm.

There was also prepared a microbicide "b" by subjecting a commercial zeolite to the same silver ion exchange. The compositions of the microbicides a and b are shown in Table 1.

TABLE 1

| Kind of microbicide | Composition |
| --- | --- |
| a | $Ag_{0.20}H_{0.20}Na_{0.60}Zr_2(PO_4)_3$ |
| b | $0.03Ag_2O \cdot 0.9Na_2O \cdot Al_2O_3 \cdot 2.0SiO_2$ |

Referential Example 2 [Preparation of Antimicrobial Fibers]

A portion of each of the microbicides a and b obtained in Referential Example 1 was mixed with a nylon 6 resin for fibers. Each of the microbicide-containing resins was subjected to melt spinning in an ordinary manner to obtain two antimicrobial fibers each of about 90 deniers (24-multifilament). There was also prepared a comparative fiber containing no microbicide, in the same manner.

In Table 2 there are shown the relations of sample Nos. of the resulting antimicrobial and comparative fibers and microbicides contained therein.

TABLE 2

| Sample No. | Kind of microbicide |
| --- | --- |
| 1 | No microbicide contained |
| 2 | a |
| 3 | b |

Example 1

[Preparation of Fiber-Treating Solutions]

0.3 part by weight of a discoloration inhibitor (potassium salt of methylbenzotriazole) was added to 100 parts by weight of an ester type spinning oil or a 10% aqueous sodium hydroxide solution, and they were thoroughly mixed, whereby a discoloration inhibitor-containing spinning oil and a discoloration inhibitor-containing alkali treating solution were prepared.

[Evaluation of discoloration inhibitor-containing spinning oil]

Each of the antimicrobial fibers and microbicide-free fiber obtained in Referential Example 2 was dipped in the discoloration inhibitor-containing ester type spinning oil and dried, then exposed to sunlight outdoors for 1 day, and visually examined for fiber discoloration.

For comparison, the same procedure was conducted using the ester type spinning oil containing no discoloration inhibitor. The thus obtained effects of the discoloration inhibitor-containing ester type spinning oil and the comparative spinning oil are shown in Table 3.

TABLE 3

| Sample No. | Microbicide | Effect (color change) | |
| --- | --- | --- | --- |
| | | Using discoloration inhibitor | Using no discoloration inhibitor |
| 1 | Not used | No discoloration | No discoloration |
| 2 | a | No discoloration | Changed to light brown |
| 3 | b | No discoloration | Changed to brown |

[Evaluation of Discoloration Inhibitor-Containing Alkali Treating Solution]

Each of the antimicrobial fibers and microbicide-free fiber obtained in Referential Example 2 was dipped in the discoloration inhibitor-containing alkali treating solution in a closed vessel. The closed vessel was kept at 121° C. for 10 minutes. Then, each fiber was taken out, washed with water and visually examined for fiber discoloration. For comparison, the same procedure was conducted using the alkali solution containing no discoloration inhibitor. The thus obtained effects of the discoloration inhibitor-containing alkali treating solution and the comparative alkali treating solution are shown in Table 4.

TABLE 4

| Sample No. | Microbicide | Effect (color change) | |
| --- | --- | --- | --- |
| | | Using discoloration inhibitor | Using no discoloration inhibitor |
| 1 | Not used | No discoloration | No discoloration |
| 2 | a | No discoloration | Changed to light yellow |
| 3 | b | No discoloration | Changed to brown |

As clear from Table 3 and Table 4, the antimicrobial fibers treated with discoloration inhibitor-containing treating solutions caused no discoloration similarly to the fiber containing no microbicide. The antimicrobial fibers treated with discoloration inhibitor-free solutions caused significant discoloration.

[Test for Antimicrobial Property]

Each of the sample Nos. 1, 2 and 3 after treatment with the discoloration inhibitor-containing ester type spinning oil or with the discoloration inhibitor-containing alkali treating solution was subjected to the following test for antimicrobial property.

Each fiber was weighed by 1 g and cut into small pieces to prepare a sample. The sample was added to 15 ml of a phosphate buffer solution placed in an Erlenmeyer flask. Thereto was added a solution of *Escherichia coli* so as to give a concentration of about $10^5$ microbes/ml. The mixture was shaked at 27° C. for 1 hour. 1 ml of the mixture was taken and cultured at 36° C. for 1 day in a standard agar medium by dilution plate culture method, after which the number of living microbes was counted. The results of the test are shown in Table 5.

TABLE 5

| Sample No. | Number of living microbes | |
| --- | --- | --- |
| | Ester type oil | Alkali treating solution |
| 1 | $4.5 \times 10^5$ | $5.0 \times 10^5$ |
| 2 | Smaller than 10 | Smaller than 10 |
| 3 | Smaller than 10 | $3.1 \times 10^2$ |

As clear from Table 5, each of the sample Nos. 2 and 3 each containing a microbicide showed an excellent antimicrobial property.

What is claimed is:

1. In a process for producing an antimicrobial fiber incorporating a silver-containing inorganic microbicide, comprising a step of passing said fiber through a liquid treating solution, the improvement wherein
said liquid treating solution contains a discoloration inhibiting effective amount of a discoloration inhibitor of the formula:

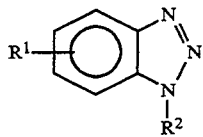

wherein $R^1$ is hydrogen or a lower alkyl group and $R^2$ is hydrogen or an alkali metal.

2. A process according to claim 1, wherein $R^1$ is methyl and $R^2$ is hydrogen or potassium.

3. A process according to claim 1, wherein the treating solution contains the discoloration inhibitor in an amount of 0.005-5 parts by weight per 100 parts by weight of the treating solution.

4. A process according to claim 1, wherein the silver-containing inorganic microbicide is an inorganic ion exchanger having silver ion supported thereon.

5. A process according to claim 4, wherein the silver-containing inorganic microbicide is represented by the following general formula:

$$Ag_p M^1_q M^2_2 (PO_4)_3 \cdot n H_2O$$

wherein $M^1$ is at least one ion selected from the group consisting of alkali metal ions, alkaline earth metal ions, ammonium ion and hydrogen ion; $M^2$ is a tetravalent metal selected from the group consisting of Ti, Zr and Sn; n is a number satisfying $0 \leq n \leq 6$; and p and q are positive numbers satisfying $p + mq = 1$ wherein m is a valence of the ion $M^1$.

6. A process according to claim 5, wherein p is 0.01 to 0.5.

7. A process according to claim 1 wherein said liquid treating solution is an oil, an aqueous alkali solution, a bleaching solution or a detergent solution.

8. A process according to claim 4, wherein the inorganic ion exchanger is selected from the group consisting of zeolite, hydroxyapatite, zirconium phosphate, titanium phosphate, potassium titanate, antimony oxide hydrate, bismuth oxide hydrate, zirconium oxide hydrate and hydrotalcite.

* * * * *